United States Patent
Berent

[11] Patent Number: 5,818,569
[45] Date of Patent: Oct. 6, 1998

[54] LITHE CLOTH SPECTACLES

[76] Inventor: Erica G. Berent, 3216 Flagstaff Ct., Las Vegas, Nev. 89117

[21] Appl. No.: 829,100

[22] Filed: Mar. 31, 1997

Related U.S. Application Data

[62] Division of Ser. No. 662,485, Jun. 13, 1996, abandoned.

[51] Int. Cl.$^6$ ........................................................ G02C 3/00
[52] U.S. Cl. .................................... 351/156; 351/41; 2/452
[58] Field of Search ................................ 351/41, 158, 157, 351/156; 2/452, 454, 426

[56] References Cited

U.S. PATENT DOCUMENTS

| | | |
|---|---|---|
| D. 207,187 | 3/1967 | Gould . |
| 3,173,147 | 3/1965 | Gross et al. . |
| 4,133,604 | 1/1979 | Fuller . |
| 4,176,410 | 12/1979 | Matthias . |
| 4,520,510 | 6/1985 | Daigle . |
| 4,616,367 | 10/1986 | Jean, Jr. et al. . |
| 4,712,254 | 12/1987 | Daigle . |
| 4,751,746 | 6/1988 | Rustin . |
| 4,790,646 | 12/1988 | Seron . |
| 4,811,430 | 3/1989 | Janusz . |
| 4,818,094 | 4/1989 | Lyons . |
| 4,852,189 | 8/1989 | Duggan . |
| 4,872,465 | 10/1989 | Kuntz et al. . |
| 5,042,094 | 8/1991 | Sadowsky . |
| 5,201,856 | 4/1993 | Edwards . |
| 5,268,710 | 12/1993 | Anstey . |
| 5,297,298 | 3/1994 | Salatka et al. . |
| 5,369,452 | 11/1994 | Williams . |
| 5,384,605 | 1/1995 | Escobosa . |

*Primary Examiner*—Hung X. Dang
*Attorney, Agent, or Firm*—Quirk & Tratos

[57] ABSTRACT

Comfortable cloth spectacles are provided having a flexible, collapsible and rollable cloth frame and an attached lithe lens membrane which can be tinted, UV protective or corrective. The frame may be fashioned from inner and outer layers of cloth material and is suitable for machine washing. Bands on the frame are adapted to encircle the head and interconnect to secure the spectacles to the head. Cushiony protuberances on the frame space the frame from the eyes.

14 Claims, 2 Drawing Sheets

5,818,569

LITHE CLOTH SPECTACLES

This application is a divisional of application Ser. No. 08/662,485, filed Jun. 13, 1996, now abandoned.

BACKGROUND OF THE INVENTION

Traditional spectacles and eyeglasses, because of their rigid nature are often uncomfortable and, in certain applications, impractical. They cannot be conveniently worn under helmets and hardhats, and in water or with perspiration such as during play of sports tend to shift, slide or fall off. Further because of the rigid frame and lenses for these spectacles, they are subject to breakage. Also, a problem exists where the spectacles are removed, such as when sunglasses are removed. When not needed the wearer must stow the glasses, carry them or set them down. The solution has been to put the spectacles in a carrying case, put the glasses up to be worn on top of the head or use a strap so that the glasses can hang around the neck. This is inconvenient and as a result glasses may be temporarily set down somewhere and lost.

Still further, traditional spectacles and glasses can be uncomfortable. Individuals may not be able to obtain glasses which conform to the face. Since the spectacles are rigid, they cannot be adjusted to conform to the face for comfortable wear.

The spectacles of the present invention are intended to substantially eliminate and solve the problems noted above by providing a flexible, conformable, machine launderable spectacles which can be rolled, folded or wadded for storage.

SUMMARY OF THE INVENTION

The present invention is directed to spectacles which may be sunglasses, corrective glasses or protective eyewear having a cloth frame for being secured around the user's face and head. A lithe lens membrane is sewn to or otherwise secured to the cloth frame at a location to be superimposed over the eyes of the wearer when the spectacles are worn. The spectacles preferably have a Velcro® or a pressure-sensitive or locking and readily releasable material for securing the spectacles around the head of the user. The edges of the lens membrane are secured to the cloth frame by stitching or the like such that there are no exposed lens edges or corners. Protuberances are provided which project from the inner surface of the cloth frame to space the lens membrane from the eyelashes when the spectacles are worn.

The spectacles are comfortable in that the flexibility enables them to conform the head of the wearer, are collapsible and rollable for folding over to put in the pocket or securing about the arm or wrist when not in use and are machine launderable.

Other advantages and features will be evident from the following detailed description.

DETAILED DESCRIPTION OF THE PREFERRED EMBODIMENT

Figure 1:
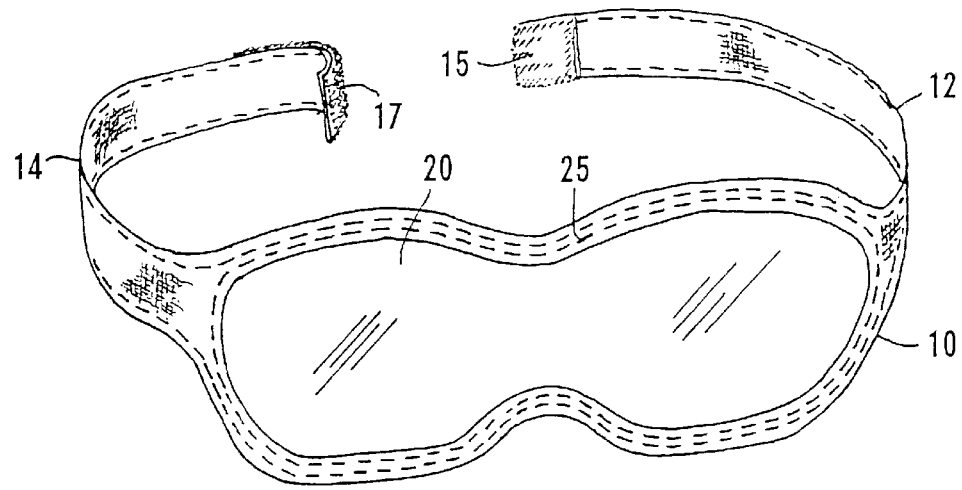
FIG. 1 is a perspective view of one embodiment of the invention using a single lens membrane.
Figure 2:
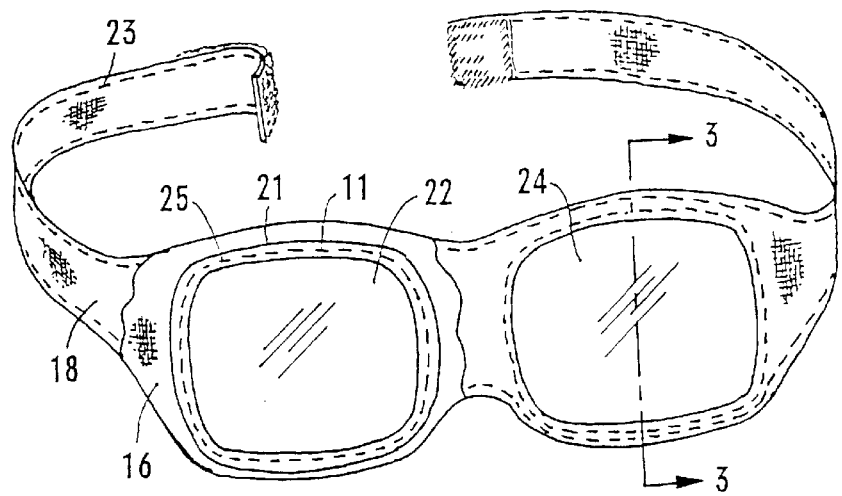
FIG. 2 is a view of a second embodiment using two lens membranes, with one layer of the cloth frame partially cut away.

As illustrated in FIGS. 1 and 2, a flexible, collapsible and rollable cloth frame 10 of the spectacles comprises a pair of opposite headband portions 12 and 14 which extend from the lens membrane securing portion of the frame 10. The ends of each of the headband portions 12, 14 terminate with means for securing opposite headband portion ends near the back of the wearer's head. Pressure sensitive and releasable locking or adhesive strips may be used on the opposing ends. A preferred means comprises Velcro® with the hook component 15 and loop component 17 on opposite headband portion ends. Other means for securing the two headband portion ends together include the use of snaps, button, hook, clasp, or pins, but are not preferred because of discomfort, and the potential for injury to the head and skin. Velcro® is preferred because it is flexible, and is easily sewn or stitched to the ends of the headband portions. Such a material also facilitates comfortable positioning of the headband portions around the user's head and may be readily locked by simply touching the frame ends together.

The frame 10 is substantially planar and is flexible, foldable, collapsible and rollable due to its cloth construction and is lightweight.

Figure 3:
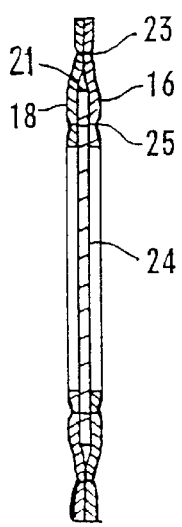
FIG. 3 is a cross-sectional view of the frame and lens membrane taken along line 3—3 of FIG. 2.

As illustrated in FIGS. 1 and 2, the lens may be a single unitary, lithe lens membrane 20 as shown in FIG. 1, or a pair of lithe lens membranes 22 and 24 as shown in FIG. 2. Regardless of which embodiment is used, the lens membranes are secured to the cloth frame member such that there is no edge or perimeter surface of a lens membrane 20 exposed to the face of the wearer. Preferably, this is achieved by fashioning the cloth frame 10 using two cloth layers, an inner layer 16 and an outer layer 18, which are stitched together with stitching 23 or other suitable sewing or fastening component or adhesive material adjacent to or along the facing edges of the two cloth layers. Observing particularly FIG. 2, lens membrane 22 is positioned such that inner cloth layer 16 lies between the face of the wearer and edge 21 of the lens membrane 20. The lens membrane material comprises a transparent, flexible, lithe material, preferably a thin, flexible plastic membrane which can be readily stitched or otherwise secured to the fabric frame. Examples of suitable lens membrane materials include polyester, acrylic, polyethylene, polypropylene, polyvinyl chloride, cellulosic polymers, especially cellulose acetate, fluoroplastics, polycarbonate, and the like. Such materials should not only be flexible but should also be non-toxic, non-flammable or incorporate flame retardants, non-irritating and preferably do not easily puncture, tear, and yet are substantially transparent. An adhesive may be used to secure the lens membrane to the frame, so long as it is quite flexible when it is dry. However, preferably, the lens membrane 20 is stitched or sewn to the cloth frame 10, to both the inner and outer layers 16, 18 where two cloth layers are used as illustrated, or to the inner layer, where only a single cloth layer is used. Stitching 25 is shown as extending around the entire edge of the lens membranes 22, 24 in FIGS. 1 and 2 for sandwiching and securing the lens membranes to the cloth frame 10. In FIG. 3, the stitching 23 for securing the two cloth layers 16 and 18 together and stitching 25 for securing lens membrane 24 to both of the layers of cloth are shown in cross-section.

As previously noted, it may be desirable to utilize only a single layer of cloth for the frame 10, in which case, the cloth will be the inner layer 16, preferably fashioned from cotton knit. In either embodiment, the size of the opening to receive the lens membranes cut or formed in the frame 10 is smaller than the size of the membrane, whereby the cloth prevents the outer peripheral edge 21 of the lens membrane from contact or exposure to the face of the wearer. Where two cloth layers are utilized, the lens membrane is sandwiched between the two cloth layers and permanently secured to both layers, either by stitching, adhesive or other suitable means.

Although the lens membrane 20 may be clear, it is preferably smoked, polarized, UV light blocking, and/or otherwise darkened to protect the eyes of the wearer from sun glare. If desired, the lens may also be manufactured or formed of a corrective lens material, so long as it is flexible and is capable of being sewn, stitched, tacked or otherwise substantially permanently secured to the inner or inner and outer layers of cloth.

The spectacles according to the present invention are extremely flexible because the frame 10 is cloth and the lens membrane 20 is lithe or flexible. When not in use the wearer can wad, roll or fold the spectacles up and put them in their pocket or can wrap or roll them about their arm or wrist like a bracelet and secure them using the fastening means. Further the flexibility of the spectacles minimizes breakage thereof. If they are sat on, for example, they win not break. Still further, because the frame 10 is cloth, the pattern and texture of the cloth can be selected to match clothing such as a bathing suit.

Still further, the spectacles are machine washable. The cloth frame 10 and lithe, flexible lens membrane 20 make the spectacles suitable to be put in a washing machine with clothes, washed and hung to dry.

The spectacles, because of the flexibility and adaption to be secured about the head are also well suited to be worn under helmets such as motorcycle helmets, hardhats or the like. They can also be use in sports to provide a degree of protection for the eyes.

The cloth of the frame 10 may be a cotton, cotton flannel or elastic cloth such as Spandex®. Where inner and outer layers 16, 18 of cloth are to be used, the inner layer is preferably a cotton or cotton flannel material to be soft on the skin while the outer layer is Spandex® or comparable elastic material.

Figure 4:
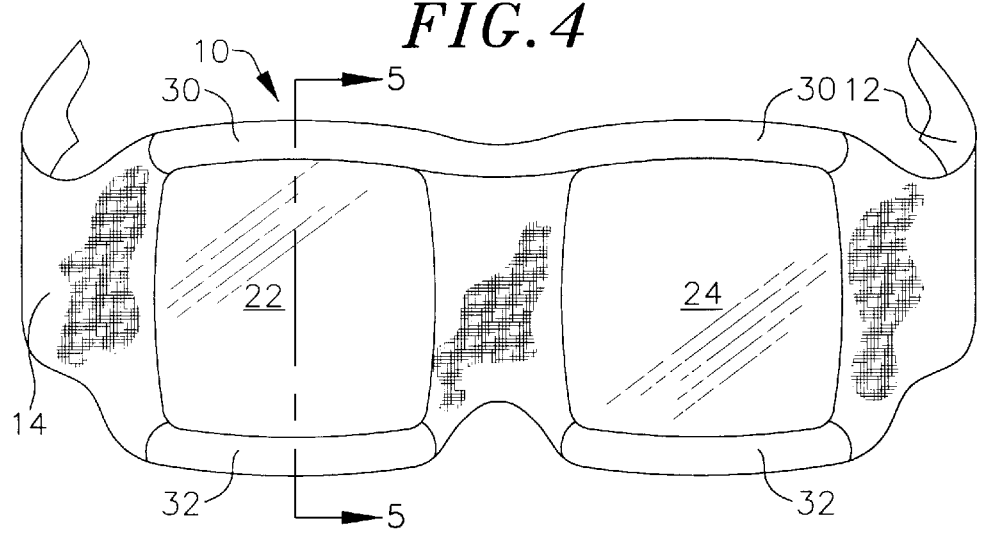
FIG. 4 is a rear view of a further embodiment of the invention.

Turning to FIG. 4 yet another embodiment of the present invention is shown. Like components will have like reference numerals.

According to this embodiment, a frame 10 is provided for mounting a single, unitary lens membrane 20 or separate lens membranes 22,24 as described above. Like the previous embodiment the lens membranes 22, 24 are of transparent, flexible, lithe material which may be clear, colored, polarized, UV blocking, corrective or the like. The cloth frame 10 includes headband portions 12,14 for securing the spectacles about the head of the user such that the lens membranes 22, 24 are positioned over the eyes.

Figure 5:
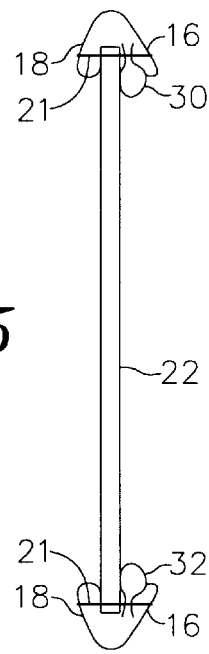
FIG. 5 is a section view along line 5—5 of FIG. 4.

As shown in FIG. 5 the frame 10 can be fashioned from cloth inner and outer layers 16,18, or a single layer folded around the lens membranes 22, 24 and sewn together by stitching 21. The stitching 21 extends through the lens membranes 22, 24 to couple the inner and outer layers 16,18 together and to attach and sandwich the lens membranes therebetween. It is to be understood that the cloth 16,18 layers could be also secured to the lens membranes 22,24 by a suitable adhesive.

To space the lens membranes 22, 24 from the eyelashes, at least one upper protuberance 30 and at least one lower protuberance 32 are provided on the inside of the frame 10 above and below the lens membranes 22, 24. Each of the protuberances 30,32 is soft, flexible and cushiony and projects from the frame 10. As shown in FIG. 4 a single upper protuberance 30 extends along the frame 10 the combined length of the lens membrane whereas a pair of lower protuberances 32 are provided below each of the lens membranes 22, 24. Each of the protuberances may be fashioned from a cotton material gathered or cotton cord and sewn by the stitching 23. The material or cord may be enveloped by the inner layer of the cloth for the frame 10. When the frame 10 is positioned about the head, the protuberances contact the face above and below the eyes to space the frame 10 from the head and hence the lens membranes 22,24 from the eyelashes. In this fashion the lens membranes 22,24 do not interfere with the blinking and eyelashes of the eyes.

Figure 6:
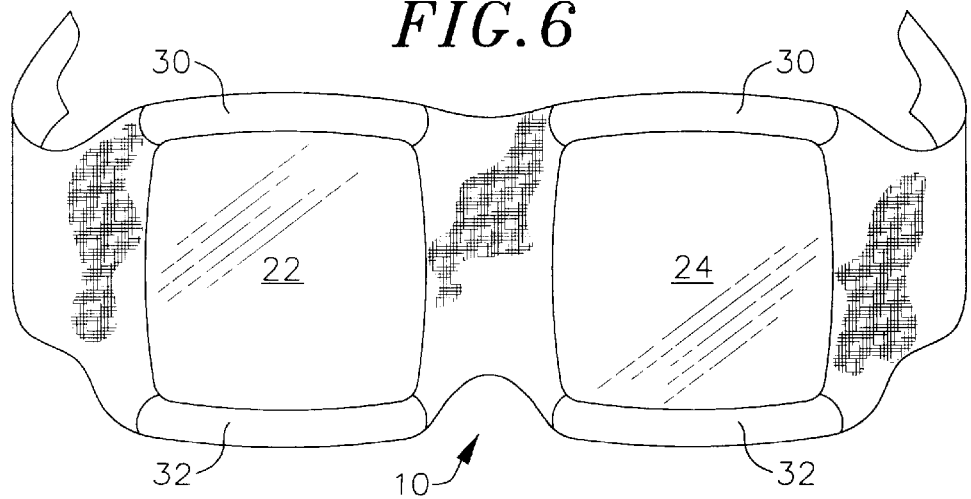
FIG. 6 is view similar to that of FIG. 4 of yet another embodiment of the invention.

FIG. 6 shows a further embodiment of the invention with a pair of upper and lower protuberances 30,32.

The specific material used for the cloth is not so critical, and may, as described above, comprise cotton, polyester, nylon and the like, or blends of two or more of such materials. Material comprising the frame and especially the inner layer, is preferably a soft or cushioned fabric, such as a cotton or cotton flannel which will not irritate the user's skin when the device is secured around the user's head. By using such soft, flexible cloth for the frame material, and using a flexible lens material as previously described, the spectacles can very comfortably conform to the wearer's head, and be secured by contacting the Velcro® end tabs of the two headband portions. As a further advantage, the protuberances provided resist the flow of moisture such as perspiration into the eyes. Such advantages as well as others will be evident to those skilled in the art.

What is claimed is:

1. Lithe cloth spectacles comprising:
    a soft, collapsible and rollable entirely cloth frame portion capable of extending entirely around a user's head;
    a lithe lens membrane permanently secured to said frame portion to be superimposed over the eyes; and
    a flexible, cushiony protuberance projecting from the frame and disposed to contact areas located above and below each eye when the spectacle are positioned about the head to space the lens membrane in front of the eyes.

2. The spectacles of claim 1 wherein said frame portion comprises first and second layers of a soft, flexible and foldable cloth material, and wherein the edge of said lens membrane is sandwiched between said first and second material layers.

3. The spectacles of claim 2 wherein said lens membrane is sewn to said first and second material layers around the periphery of said lens membrane.

4. The spectacles of claim 2 wherein said lens membrane is secured to said first and second material layers with adhesive.

5. The spectacles of claim 1 wherein said lens membrane is selected from a group including one or more of smoked transparent membrane, tinted transparent membrane, ultraviolet ray filtering membrane, polarized transparent membrane or corrective lens membrane.

6. The spectacles of claim 1 wherein said frame portion includes a pair of opposite bands, each of said bands having a releasable means adjacent an end of said band for being secured to the other of said bands when the bands are wrapped about the head to secure the spectacles thereto.

7. The spectacles of claim 1 wherein said frame includes an outer cloth layer of a first material and an inner layer of a second material.

8. The spectacles of claim 7 wherein the outer cloth layer is and elastic cloth material and the inner layer is a soft cotton material.

9. Spectacles comprising:

- a soft, flexible, substantially planar and entirely cloth frame portion adapted to be secured about the user's head;
- least one lithe lens membrane permanently secured to the frame, said lens positioned to overlay the eyes when the frame is secured about the user's head; and
- a flexible, cushiony protuberance disposed on the frame above and below the lens membrane and projecting from the frame to contact the face to space the lens from the eyelashes.

10. The spectacles of claim 9 wherein said frame includes an outer cloth layer of a first material and an inner cloth layer of a second material.

11. The spectacles of claim 10 wherein the outer cloth layer is an elastic cloth.

12. The spectacles of claim 11 wherein the inner cloth layer is a cotton cloth.

13. The spectacles of claim 12 wherein the cotton fabric is a cotton flannel.

14. The spectacles of claim 9 including a pair of upper protuberances each disposed to be located one above each eye and a pair of lower protuberances each disposed to be located one below each eye.

* * * * *